United States Patent [19]

Pieniak et al.

[11] Patent Number: 5,451,442
[45] Date of Patent: Sep. 19, 1995

[54] ABSORBENT PANEL STRUCTURE FOR A DISPOSABLE GARMENT

[75] Inventors: Heinz A. Pieniak, Des Moines; Gloria Huffman, Federal Way, both of Wash.

[73] Assignee: Paragon Trade Brands, Inc., Federal Way, Wash.

[21] Appl. No.: 49,138

[22] Filed: Apr. 19, 1993

Related U.S. Application Data

[63] Continuation-in-part of Ser. No. 809,052, Dec. 17, 1991, abandoned.

[51] Int. Cl.⁶ .................. B32B 3/10; B32B 3/30; A61F 13/20
[52] U.S. Cl. .................. 428/54; 428/167; 428/218; 428/283; 428/290; 604/374; 604/379; 604/380; 604/385.1
[58] Field of Search .................. 428/54, 167; 604/374, 604/379, 380, 385.1

[56] References Cited

U.S. PATENT DOCUMENTS

| | | | |
|---|---|---|---|
| Re. 29,789 | 10/1978 | Kolbach | 128/284 |
| 1,976,282 | 2/1932 | Izumiyama | 154/44 |
| 3,017,304 | 1/1962 | Burgeni | 154/54 |
| 3,612,055 | 10/1971 | Mesek | 128/287 |
| 3,661,154 | 5/1972 | Torr | 128/284 |
| 3,670,731 | 6/1972 | Harmon | 128/284 |
| 3,766,922 | 10/1973 | Krusko | 128/284 |
| 3,769,978 | 11/1973 | DeNight | 128/284 |
| 3,848,598 | 11/1974 | Mesek | 128/287 |
| 3,938,522 | 2/1976 | Repke | 128/287 |
| 4,102,340 | 7/1978 | Mesek et al. | 128/287 |
| 4,103,062 | 7/1978 | Aberson et al. | 428/283 |
| 4,186,165 | 1/1980 | Aberson et al. | 264/112 |
| 4,235,237 | 11/1980 | Mesek et al. | 128/284 |
| 4,364,992 | 12/1982 | Ito et al. | 428/283 |
| 4,381,782 | 5/1983 | Mazurak et al. | 604/368 |
| 4,624,666 | 11/1986 | DeRossett et al. | 604/366 |
| 4,670,011 | 6/1987 | Mesek | 604/378 |
| 4,673,402 | 6/1987 | Weisman et al. | 604/368 |
| 4,685,915 | 8/1987 | Hasse et al. | 604/378 |
| 4,699,619 | 10/1987 | Bernardin | 604/378 |
| 4,834,735 | 5/1989 | Alemany et al. | 604/368 |
| 4,840,692 | 6/1989 | Kamstrup-Larsen | 156/252 |

FOREIGN PATENT DOCUMENTS

| | | |
|---|---|---|
| 439962A1 | 8/1991 | European Pat. Off. |
| 1406615 | 9/1975 | United Kingdom |
| WO86/01378 | 3/1986 | WIPO |

*Primary Examiner*—George F. Lesmes
*Assistant Examiner*—Kathryne E. Shelborne
*Attorney, Agent, or Firm*—Dressler, Goldsmith, Shore & Milnamow, Ltd.

[57] ABSTRACT

Absorbent panel structures that comprise a unitary pulp panel having a forward section and a rearward section, the rearward section comprising from about 20% to about 70% of the rearward panel length. One or more longitudinally elongated areas or grooves of reduced thickness and basis weight are formed in the panel. The rearward section preferably has a mean basis weight that is from about 30% to about 70% less than the mean basis weight of the forward section of the panel. The thickness of the elongated areas may be uniform along the length of the panel or may decrease along the panel length direction from the front edge to the rear edge. Superabsorbent particles may be uniformly dispersed throughout the panel or may be dispersed in longitudinal stripes that may or may not coincide with the elongated areas.

18 Claims, 5 Drawing Sheets

ABSORBENT PANEL STRUCTURE FOR A DISPOSABLE GARMENT

CROSS-REFERENCE TO RELATED APPLICATION

This case is a continuation-in-part of application Ser. No. 07/809,052 filed Sep. 17, 1991, now abandoned.

FIELD OF THE INVENTION

The present invention relates to new and improved pulp-containing absorbent structures for use in a disposable diaper or the like, that effectively and efficiently utilize the materials disposed therein, including superabsorbent materials, in a cost effective manner.

BACKGROUND OF THE INVENTION

Disposable absorbent products have been known for some time, including such products as disposable diapers, sanitary wound dressings, bandages, incontinent pads, and the like. These products incorporate an absorbent batt or panel that is used to absorb and hold or contain body fluids. In years past, in many of these products, especially diapers and sanitary napkins, the absorbent batt comprised what is termed "wadding" or plies of tissue. The wadding was disposed between an impermeable backing sheet and a permeable facing sheet and the plies of tissue were used to absorb and contain the liquid within the product.

The wadding type of batt was replaced, for the most part, by an improved absorbent batt comprised of fluffed wood pulp fibers. This absorbent batt comprises a layer of individualized wood pulp fibers with the layer having substantial thickness. This diaper has improved absorbent capacity and has somewhat better containment than a diaper using a wadding layer. Also the fluffed wood pulp layer is quite soft, flexible and conformable and hence, produces an improved diaper over diapers using wadding as the absorbent layer.

Though the fluffed wood pulp absorbent batts have improved capacity, the efficiency with which the capacity is used in a diaper is poor. The reason for this, is that the fluid to be absorbed is generally deposited in a localized or a target area within the absorbent batt and the ability for the fluid to wick along the plane of the batt is poor. The fluid follows the path of least resistance and consequently moves to the closest edge of the batt where it generally is no 10 longer contained and the product leaks. Furthermore, the wood pulp batts lack stability, e.g., when a diaper is being worn, the batt tends to sag and/or break up thereby creating bunching.

U.S. Pat. No. 3,017,304 discloses an absorbent product which incorporates in the batt a densified, paper-like layer. This paper-like layer acts as a wick, i.e., liquid which contacts the layer tends to move rapidly along the plane of the layer. When incorporated in combination with fluffed wood pulp fiber, the resultant product uses the absorbent capacity of the fluffed wood pulp much more efficiently. Diapers which incorporate this paper-like layer combined with fluffed wood pulp are disclosed and described in U.S. Pat. Nos. 3,612,055 and 3,938,522. Even though these products make much greater use of the capacity of the absorbent batt, they still do not totally contain the absorbed liquid.

A number of years ago "superabsorbent materials", i.e., materials which will absorb many times their weight of liquid, were developed. Since the development of such materials, various different approaches have been suggested to incorporate them in absorbent products such as diapers to enhance the absorptive performance of these products. Perhaps one of the first proposals to incorporate such a superabsorbent material in a disposable diaper is disclosed in U.S. Pat. No. 3,670,731. This patent discloses an absorbent dressing comprising an absorbent layer sandwiched between a permeable facing sheet and an impermeable backing sheet. The absorbent layer contains water insoluble cross-linked hydrocolloid polymer as the superabsorbent material.

In order for a superabsorbent material to function, the liquid being absorbed must be transported 10 to the superabsorbent material. In other words, the superabsorbent material must be placed in a position to be contacted by the liquid discharged onto the absorbent body. Furthermore, as the superabsorbent material absorbs the liquid, it must be allowed to swell. If the superabsorbent is prevented from swelling, it will cease absorbing liquid. Hence, if the superabsorbent material is to function in diapers wherein the liquid to be absorbed is discharged in a small void area, the structure of the absorbent layer containing superabsorbent materials appears to be critical. Over the years a number of techniques have been disclosed in an attempt to provide structures which make efficient use of the superabsorbent material. Such products are typified by those disclosed in U.S. Pat. Nos. 4,103,062, 4,102,340 and 4,235,237. In addition, methods for incorporating superabsorbents into suitable layers or suitable configurations which can be placed in an absorbent product have been proposed, and examples of such proposals are disclosed in U.S. Pat. Nos. 4,186,165, 4,340,057 and 4,364,992.

In United Kingdom Patent Specification No. 1,406,615, published on Sep. 17, 1975, an absorbent pad for use in a disposable diaper is disclosed that includes a wood pulp batt of substantially uniform thickness having a gelling agent or superabsorbent material impregnated in one part (target area) of the batt to the exclusion of, or to a greater extent than in, another part of the batt. In accordance with a preferred embodiment, the superabsorbent material is impregnated in a central area of the pad where it is most effective rather than spreading the material evenly throughout the pad area which is deemed to be uneconomical. The weight of the superabsorbent material in the central area is disclosed as being between 20 percent and 100 percent of the weight of the pad in the central area before impregnation.

In U.S. Pat. No. 3,661,154, an absorbent structure for use in a disposable diaper is disclosed that includes a layer of a blend of cellulose fibers and superabsorbent material. The superabsorbent material concentration is disclosed as being about 1 to 50 parts per 100 parts of cellulose fibers. In accordance with a disclosed embodiment, an additional layer of the cellulose fibers or a layer of a blend of cellulose fibers and superabsorbent material is superimposed on the base layer. This additional layer may be narrower than the base layer and it may be disposed along the central portion of the diaper at the area most likely to be wetted (target area). The additional layer may be the same thickness as, or thicker or thinner than, the base layer.

In U.S. Pat. No. 4,381,782, an absorbent panel is disclosed that includes a web or batt of a low-density, highly absorbent filler material, such as fluff, to which superabsorbent material is incorporated thereinto in a central area near the front edge of the panel. The side portions of the panel are cut and folded over the central area of the panel.

More recently, other very similar absorbent structures that are directed to making efficient use of the superabsorbent material are disclosed in U.S. Pat. Nos. 4,699,619, 4,673,402 and 4,685,915. In U.S. Pat. No. 4,699,619 various absorbent structure embodiments are disclosed which comprise at least two layers of cellulosic fibers of different densities, with the higher density layer lying beneath a back portion of the lower density layer. In certain embodiments a layer of superabsorbent material is located beneath the higher density layer. In U.S. Pat. No. 4,673,402 an absorbent structure is disclosed that includes an upper layer of essentially hydrophilic fiber material and a lower layer of a substantially uniform combination of hydrophilic fiber material and discrete particles of substantially water-insoluble hydrogel material. The lower layer is positioned such that at least about 75% of the hydrogel material in the lower layer is found within the front two-thirds section of the absorbent structure and such that at least about 55% of the total hydrogel material in the lower layer is found within the front half section of the absorbent structure. In U.S. Pat. No. 4,685,915 an absorbent structure is disclosed that includes a layer of cellulosic fibers which is so disposed that the central portion has a greater average density per unit area and a greater average basis weight per unit area than each of the end portions. Hydrogel particles may be either uniformly dispersed or may be dispersed primarily or only in the central portion of the absorbent structure.

It has heretofore been proposed to provide absorbent panels for disposable diapers that have predetermined regions of increased fiber basis weight. In U.S. Pat. No. 3,848,598 an absorbent batt is disclosed that is made of cellulosic fibers and formed convexly about the transverse and longitudinal medians thereof. In U.S. Pat. No. 3,766,922 gender specific absorbent structures are disclosed that are made of cellulosic fibers and have predetermined regions of differing fiber basis weight. Valleys and/or ridges are embossed in certain of the regions. In U.S. Re. No. 29,789 an absorbent structure is disclosed having a medial portion of greater basis weight than flanking end and side portions. In U.S. Pat. No. 4,971,852 a cellulosic fiber-containing absorbent batt is disclosed that is longitudinally and transversely contoured by the use of a scarfing roll. There is no disclosure or teaching of forming longitudinally elongated grooves in the batt.

In U.S. Pat. No. 4,670,011 an absorbent batt is disclosed that includes upper and lower fibrous webs superposed to define a web interface therebetween. Superabsorbent particles are disposed in discrete longitudinally spaced apart regions at the interface.

In published PCT Application PCT/DK85/00081 (WO86/01378) a fibrous absorbent pad is disclosed that has a plurality of rectilinear and parallel channels that extend over the entire length of the structure. The channels are disclosed as being formed by cutting or milling and having a depth of 65–95% of the thickness of the pad.

SUMMARY OF THE INVENTION

The absorbent panel structures in accordance with the invention comprise a unitary wood pulp or cellulosic fiber panel having a forward section and a rearward section, the rearward section comprising from about 20% to about 70% of the rearward panel length. At least one longitudinally elongated area of reduced thickness and basis weight, that is laterally bounded by areas of increased thickness and basis weight, is formed in the panel. The rearward section preferably has a mean basis weight that is from about 30% to about 70% less than the mean basis weight of the forward section of the panel.

In accordance with certain preferred embodiments of the invention there are at least two transversely spaced apart longitudinally elongated areas of reduced thickness and basis weight formed in the panel. These elongated areas may be formed by a scarfing roller that scarfs out material to form scarfed grooves during manufacture of the panel. The thickness of the elongated areas may be uniform along the length of the panel or may decrease along the panel length direction from the front edge to the rear edge.

In accordance with other preferred embodiments of the invention superabsorbent particles may be dispersed in the pulp fibers. The superabsorbent particles may be uniformly dispersed throughout the panel or may be dispersed therein in a preselected pattern. The superabsorbent particles may be dispersed in stripes or bands along the length of the panel in such a way that some or all of the elongated areas coincide with the stripes of superabsorbent particles.

In other preferred embodiments of the invention, the elongated areas extend either over the entire length of the panel, or along from about 70% to about 90% of the panel's central section. In these embodiments it is preferred that the superabsorbent particles be pulsed in stripes or bands that extend along from about 50% to about 80% of the frontal section of the panel and that the elongated areas do not coincide with the superabsorbent deposition pattern.

The basis weight of the fibrous panel prior to formation of the elongated areas may be uniform from the front to the rear sections of the panel or the basis weight of the front section may be greater than that of the rear section. In the latter instance, the mean basis weight of the frontal section, comprising from about 50% to about 80% of the frontal portion of the panel, is preferably from about 1.5 to about 4.0 times greater than the mean basis weight of the rear section. The superabsorbent particles are preferably applied in spaced apart stripes that extend along the front section of the panel and the elongated areas extend over either the entire length or over a central between about 70% to about 90% section of the panel and do not coincide with the superabsorbent stripes.

A disposable diaper constructed in accordance with a preferred embodiment of the invention includes a liquid impermeable backing sheet and a liquid permeable facing sheet. An absorbent panel constructed in accordance with the invention is disposed between the backing sheet and the facing sheet. The absorbent panel may be wrapped in a tissue layer. The scarfed grooves may be embossed and adhesively laminated to the tissue and the tissue in turn may be laminated to the facing sheet.

The absorbent panels constructed in accordance with the invention are cost effective as more of the absorbent capacity is located in the vicinity of the infant voiding zone. Disposable diapers employing such absorbent panels have improved fit as the elongated grooves tend to act as folding, corrugating lines when the diaper is applied to an infant. The absorbent panels further allow easy modification to accommodate the different anthropometric needs for male and female infants with regards to optimization of location and area of absorptive capacity.

The present invention provides a new and improved absorbent panel structure for use in a disposable diaper, or the like, that provides efficient utilization of the absorptive capacity of the pulp and superabsorbent material in a cost effective manner.

Numerous other advantages and features of the present invention will become readily apparent from the following detailed description, the appended drawings, and the accompanying claims.

DETAILED DESCRIPTION OF PREFERRED EMBODIMENTS

While the present invention is susceptible of embodiment in various forms, there is shown in the drawings and will hereinafter be described various presently preferred embodiments of the invention, with the understanding that the present disclosure is to be considered as an exemplification of the invention, and is not intended to limit the invention to the specific embodiments illustrated and described herein.

As used in the present disclosure, the term diaper is intended to refer to an absorbent article that is worn by an individual for absorbing and containing urine and/or fecal matter. It is to be understood that diapers embodying the principles of the present invention may be appropriately sized for use by infants and can further be sized for use by incontinent adults.

Referring now to the drawings, therein is illustrated in FIGS. 1–6 an exemplary disposable diaper 10 embodying an absorbent panel in accordance with the principles of the present invention. Diaper 10 includes a facing layer or top sheet 12 formed of moisture pervious material, with the facing layer being adapted for positioning adjacent to the wearer of the diaper. The diaper further includes an absorbent panel structure 14, which in the illustrated embodiment, is generally T-shaped, but which may be otherwise shaped, such as hourglass-shaped, rectangular, I-shaped, or otherwise contoured. As will be further described, absorbent panel structure 14 in accordance with the invention preferably comprises a highly porous cellulosic fibrous web or layer 16, which may or may not contain superabsorbent particles dispersed therein. Fibrous web 16 has at least one longitudinally elongated area 40 of reduced thickness and basis weight formed in a rearward section of the panel.

Figure 1:
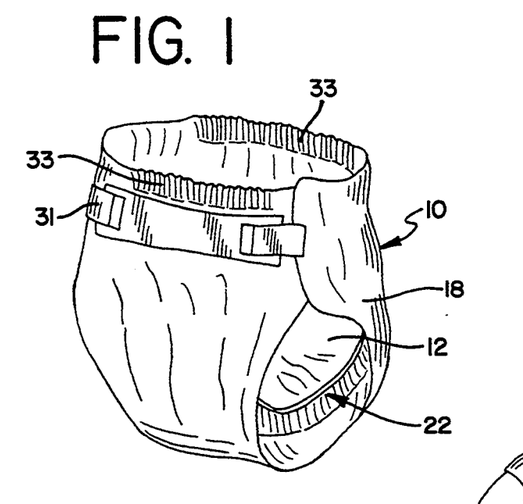
FIG. 1 is a perspective view of an exemplary disposable diaper in a completely assembled condition of the type intended to include an absorbent panel structure constructed in accordance with the principles of the present invention.
Figure 2:
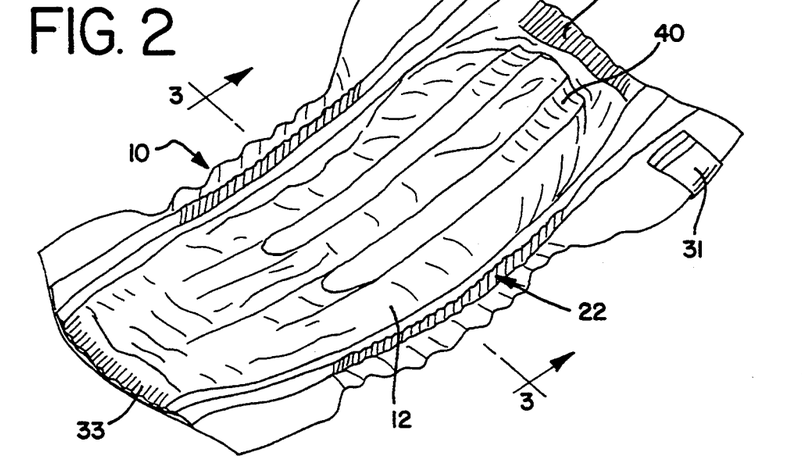
FIG. 2 is a perspective view of the diaper shown in FIG. 1 in an unfolded condition showing the top side thereof.
Figure 3:
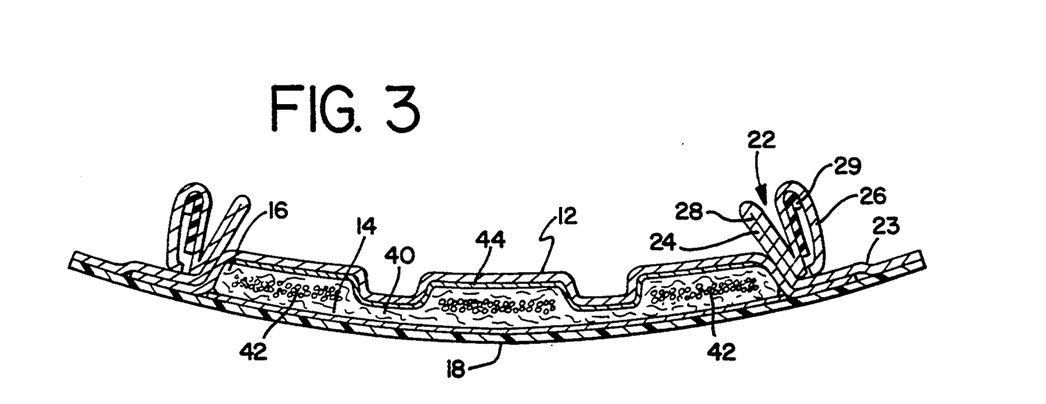
FIG. 3 is an enlarged cross-sectional view taken along line 3—3 in FIG. 2.

Disposable diaper 10 further includes a backing sheet 18 positioned on the side of the absorbent panel structure 14 that is opposite the facing layer 12. The backing sheet typically comprises a moisture-impervious material, such as plastic film or sheet. Diaper 10 may be provided with a double standing gather 22 consisting of an inner gather 24 and outer gather 26. Double standing gather 22 is preferably formed at the leg openings from a sheet of non-woven hydrophobic material 23 having vapor permeability characteristics, e.g. a fibrous non-woven fabric treated with silicone resin. Inner gather 24 is preferably elasticized by a monofilament rubber element 28 extending the length thereof and outer gather 26 is preferably elasticized by a folded polyurethane foam elastic material 29 extending the length thereof. Sheet 23 is preferably glued to backing sheet 18 by lines of hot melt adhesive.

As will be recognized by those familiar with the art, several different types of facing materials may be used for facing layer 12. For example, these layers may comprise a non-woven web made of a mixture of fibers consisting predominantly of inexpensive, short, cellulosic fibers, such as wood pulp fibers or cotton linters, with the remainder of the mixture being textile length fibers. The non-woven webs may also be formed from polyester, polyethylene, polypropylene, nylon, rayon, or the like. The facing layer may be a laminate of one or more non-woven fabrics, each having differing physical properties. The facing layer may further be apertured.

In order to secure the diaper in position, adhesive tape fasteners 31, as are well-known in the art, are provided on the rearward portions of the diaper. Each of these fasteners 31 include a tab-like element having pressure-sensitive adhesive thereon which, when brought into contact with a landing area associated with the forward, outer waist portion of the diaper, secures the diaper in position. The diaper may also be provided with elasticized waistbands 33, as are well-known in the art.

In order to most effectively utilize the absorbent capacity of the absorbent panel and to improve the fit and application of the diaper, it is desirable to provide a diaper that locates more of the absorbent capacity in the vicinity of the infant voiding zone and which provides folding or corrugating lines to enhance conformance of the diaper to the contour of the infant. The present invention is particularly directed to various unique absorbent panel structures for use in a diaper construction that possess these characteristics.

The various absorbent panel embodiments of the invention include a highly porous web 16. Web 16 is preferably formed of loosely compacted short cellulose fibers, such as wood pulp fibers, or cotton linters, or mixtures thereof, which primarily are held together by interfiber bonds, as is known in the art. Most preferably web 16 is a low bulk density coherent web of loosely compacted cellulose fibers, preferably comminuted wood pulp fibers, in the form of so-called "fluff."

The term "interfiber bonds" as used in the specification and claims is intended to mean fibers that are held together in an assemblage or batt solely by fiber-to-fiber frictional contact, and specifically excludes fibers which are held together in an assemblage or batt by extraneous means, such as heat fusion, adhesive bonding, etc. Such an assemblage of fibers may include superabsorbent particles.

Absorbent panel 14 has a forward section 34 and a rearward section 36. Rearward section 36 comprises from about 20% to about 70% of the rearward length of the panel. In accordance with the broad concepts of the invention, at least one transversely spaced apart elongated grooved area 40 is formed in the rearward section of the panel. The elongated areas 40 may be formed by scarfing out material from the web 16 by scarfing rollers or the like. The elongated areas 40 have a reduced thickness and basis weight. The elongated areas 40 may be devoid or substantially devoid of material, as shown in phantom lines in FIGS. 4 and 6. As used herein, the phrase reduced thickness and Basis weight", with reference to the elongated areas, is intended to include instances where the elongated areas are substantially devoid of fibers.

Figures 4, 5, 6, 7, 8, 9, 10:
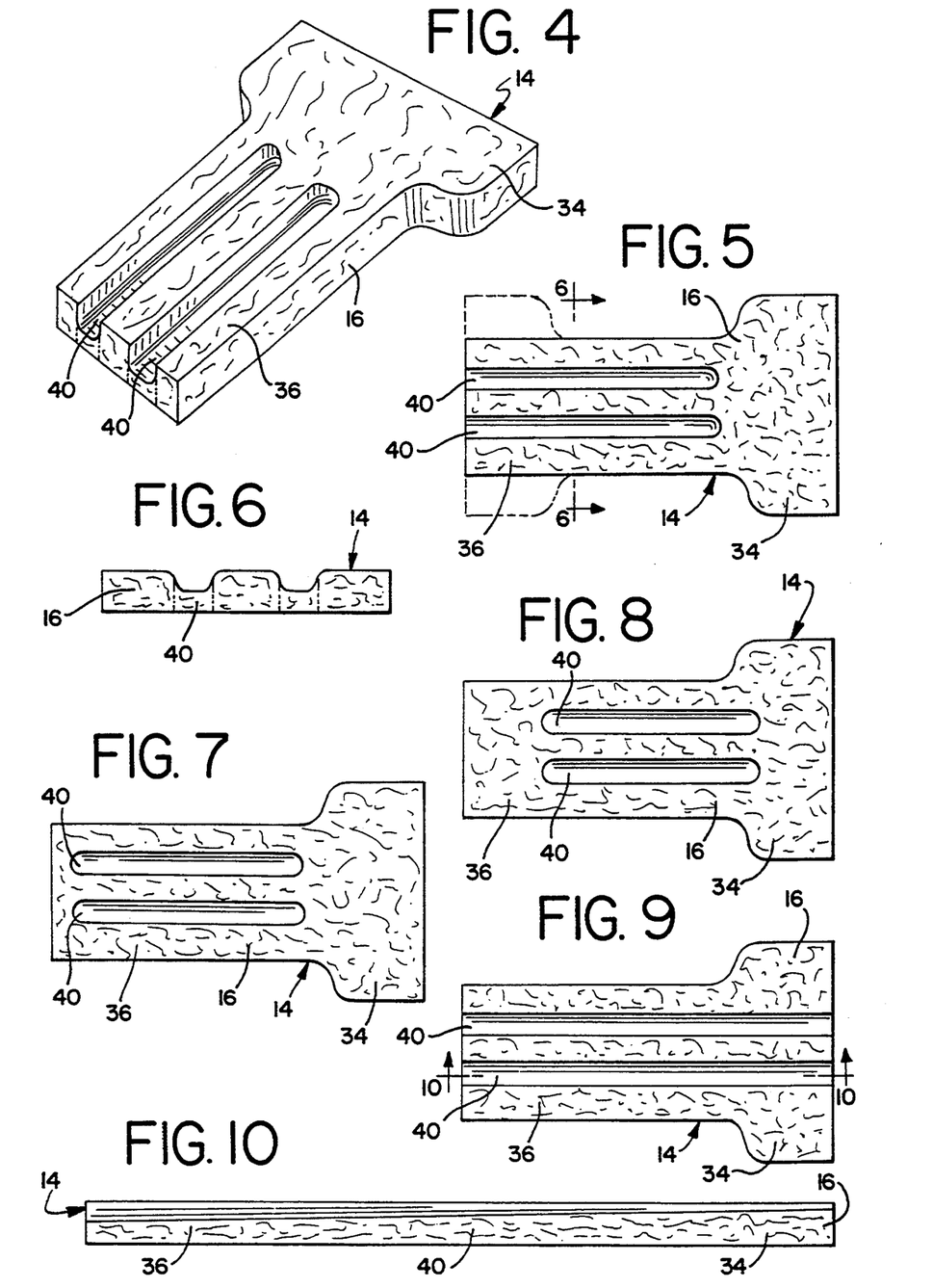
FIG. 4 is a perspective view of a first preferred embodiment of an absorbent panel structure in accordance with the invention.
FIG. 5 is a top plan view of the absorbent structure shown in FIG. 4.
FIG. 6 is an end view of the absorbent structure shown in FIG. 4.
FIG. 7 is a top plan view of a second preferred embodiment of an absorbent panel structure in accordance with the invention.
FIG. 8 is a top plan view of a third preferred embodiment of an absorbent panel structure in accordance with the invention.
FIG. 9 is a top plan view of a fourth preferred embodiment of an absorbent panel structure in accordance with the invention.
FIG. 10 is a an enlarged cross-sectional view taken along line 10—10 in FIG. 9.

The elongated areas are formed so as to create an absorbent panel wherein the rearward section 36 has a mean basis weight that is from about 30% to about 70% less than then the mean basis weight of the forward section 34 that is forward of the rearward section. As best seen in FIGS. 4 and 5, the elongated areas 40 in this embodiment extend to the rear edge of the absorbent panel. The elongated areas 40 have a thickness that is substantially uniform or equal over the entire length thereof and the basis weight of the forward portion 34 and the basis weight of the rearward portion 36 that does not include the elongated areas is substantially the same.

While the panel is shown as being generally T-shaped, it may be I-shaped, as shown in phantom lines in FIG. 5, or otherwise configured in a well known manner.

Referring to FIG. 7, in accordance with a second embodiment of the invention, the elongated areas 40 formed in the absorbent panel 40 terminate a short distance from the rear edge of the panel.

Referring to FIG. 8, in accordance with a third embodiment of the invention, the elongated areas 40 extend along a section of the panel that is intermediate the front and rear edges thereof, and is approximately from about 70% to about 90% of the length of the panel.

In accordance with a fourth preferred embodiment of the invention, the elongated areas 40 extend along substantially the entire length of the panel, as shown in FIGS. 9–10. In this embodiment, the thickness of the elongated areas 40 decrease as they extend toward the rear edge of the panel.

As is well known in the art, in order to increase the absorbent capacity of the panel, superabsorbent material may be dispersed into the fibrous web 16 that forms the panel 14. Superabsorbent material present in the web is generally a water-insoluble but water-swellable polymeric substance capable of absorbing water in an amount that is at least 10 times the weight of the polymeric substance in its dry form. The superabsorbent material is in the form of 10 particles which may be in the shape of fibers, spheres, bits of film, globules, or the like.

In one type of superabsorbent material, the particles or fibers may be described chemically as having a backbone of natural or synthetic polymers with hydrophilic groups or polymers containing hydrophilic groups being chemically bonded to the backbone or in intimate admixture therewith. Included in this class of materials are such modified natural and regenerated polymers as polysaccharides including, for example, cellulose and starch and regenerated cellulose which are modified by being carboxyalkylated, phosphonoalkylated, sulphoalkylated or phosphorylated to render them highly hydrophilic. Such modified polymers may also be cross-linked to improve their water-insolubility. These same polysaccharides may also serve, for example, as the backbond onto which other polymer moieties may be bonded by graft copolymerization techniques.

In addition to modified natural and regenerated polymers, the hydrocolloid particle component may comprise wholly synthetic hydrophilic particles. Examples of those now known in the art are polyacrylonitrile fibers which may be modified by grafting moieties thereon such a polyvinyl alcohol chains, polyvinyl alcohol itself, hydrophilic polyurethane, poly(alkylphosphonates), partially hydrolyzed polyacrylamides (e.g., poly(N-N-dimethyl acrylamide), sulfonated polystyrene, or a class of poly(alkylene oxide). These highly hydrophilic synthetic polymers may be modified by other chemical treatments such as cross-linking or hydrolysis. Further examples known in the art are the nonionic hydrophilic polymers such as polyoxethylene, polyoxpropylene and mixtures thereof which have been suitably cross-linked, either chemically or by irradiation. Still another more recent type is derived of isobutylene-maleic anhydride copolymer.

In addition, naturally occurring materials such as gums, may be used. For instance, guar gum is suitable.

If the superabsorbent material is a powder it may be sprinkled onto the fibrous web either in dry form or the web may be moistened. If the superabsorbent is in granular form it may be desirable to slightly moisten the superabsorbent before placing it in contact with the web.

Any superabsorbent material that absorbs large amounts of liquids is suitable for use in the absorbent web 16 of the present invention.

Figure 11:
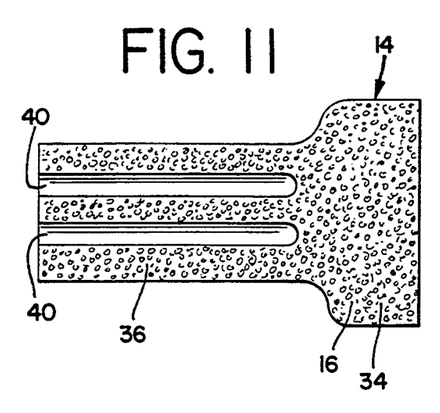
FIG. 11 is a top plan view of a fifth preferred embodiment of an absorbent panel structure in accordance with the invention.

Referring to FIG. 11, in accordance with a fifth preferred embodiment of the invention, superabsorbent particles are uniformly dispersed over substantially the entire area of web 16 that forms panel 14. As shown in FIG. 11, the elongated areas 40 extend to the rearward edge. Alternatively, the elongated areas 40 may be formed as shown in FIGS. 7, 8 or 9. Preferably, the superabsorbent particles are uniformly dispersed only along the length and crotch area (center width) of the panel. In so doing, the superabsorbent particles are concentrated in the central target area of the panel.

Figure 12:
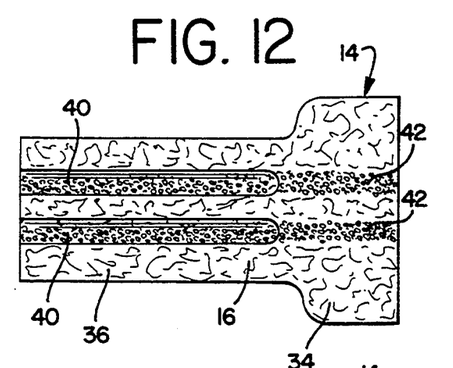
FIG. 12 is a top plan view of a sixth preferred embodiment of an absorbent panel structure in accordance with the invention.

In accordance with more effective embodiments of the invention, the superabsorbent particles may be dispersed in spaced apart stripes or bands 42 along the length of the panel. The superabsorbent particles are preferably homogeneously mixed throughout the pad thickness. Referring to FIG. 12, in accordance with a sixth preferred embodiment of the invention, the superabsorbent stripes 42 are positioned in such a way that some or all of them coincide with the elongated areas 40. The material removed by the scarfing roller is preferably recycled and reused. In so doing, the relative concentration of superabsorbent particles in the rearward portion of the panel is reduced, thus concentrating the majority of the superabsorbent particles in the forward portion of the panel where it is most effectively utilized. The absorbent panel so formed contains a low percentage of superabsorbent particles which are uniformly distributed in stripes or bands with a heavy concentration thereof in the front portion of the absorbent panel.

Figures 13, 14, 15, 16:
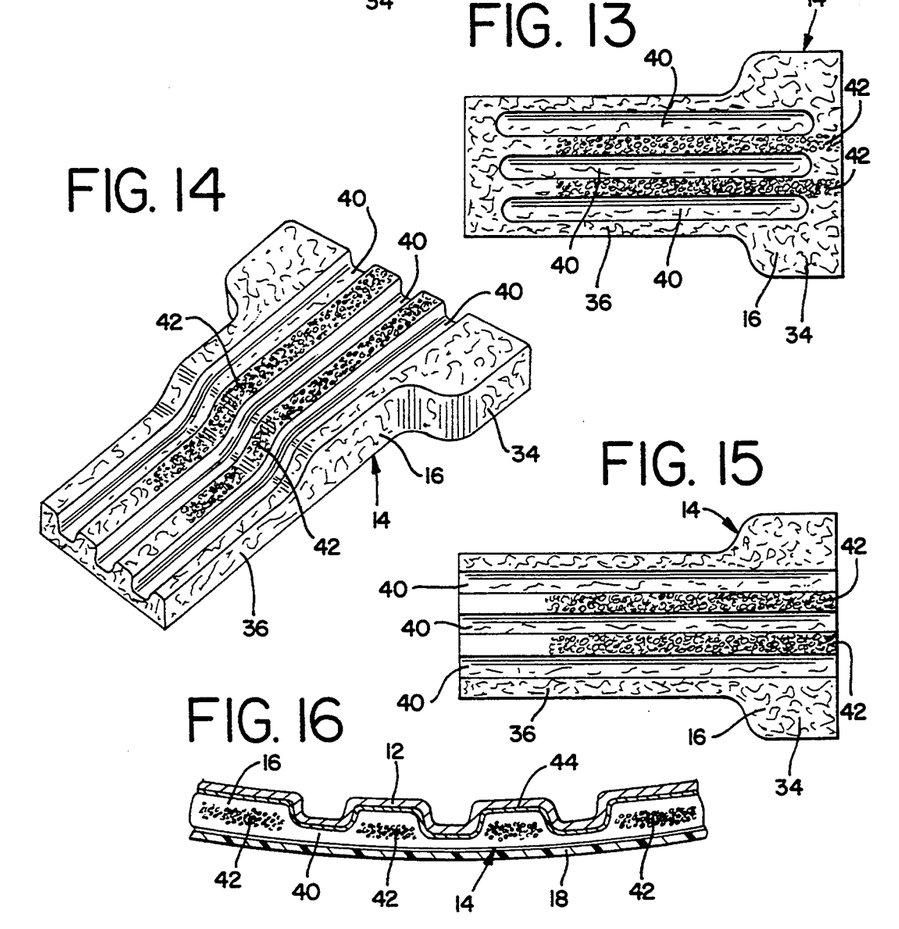
FIG. 13 is a top plan view of a seventh preferred embodiment of an absorbent panel structure in accordance with the invention.
FIG. 14 is a perspective view of an eighth preferred embodiment of an absorbent panel structure in accordance with the invention.
FIG. 15 is a top plan view of the preferred embodiment of an absorbent panel structure shown in FIG. 14.
FIG. 16 is an enlarged transverse cross-sectional view taken through an exemplary diaper construction incorporating the absorbent panel structure shown in FIGS. 14 and 15.

In accordance with other preferred embodiments of the invention, the elongated areas 40 may be extended over the entire length of the absorbent panel or along approximately from about 70% to about 90% of a longitudinal central section of the panel. As shown in FIG. 13, in order to maintain functionality and cost effectiveness of these embodiments, it is preferable that the superabsorbent particles be pulsed in stripes or bands 42 along approximately from 50% to about 80% of the front portion of the panel and the elongated areas 40 do not coincide with the superabsorbent stripes 42. In so doing, the front portion of the panel maintains its required high liquid holding capacity.

Extending the above concept even further, in accordance with an eighth preferred embodiment of the invention, it is preferred to form the absorbent web 16 with from about 1.5 to about 4.0 times more pulp fibers in terms of basis weight in the forward from about 50% to about 80% portion of the absorbent panel length. Referring to FIGS. 14 and 15, the superabsorbent particles are preferably applied in stripes or bands 42 located in this heavier basis weight region. The elongated areas 40 are formed in panel over its entire length or over from about 70% to about 90% of a central longitudinal section of the panel. The elongated areas 40 preferably do not coincide with the superabsorbent material stripes 42.

Figure 17:
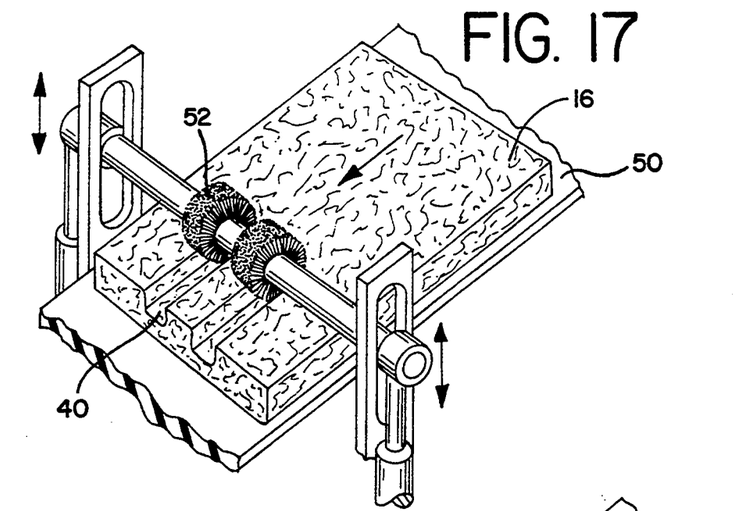
FIGS. 17–21 are schematic perspective views that illustrate alternative methods of forming an absorbent panel having elongated areas in accordance with the invention.
Figures 18, 19:
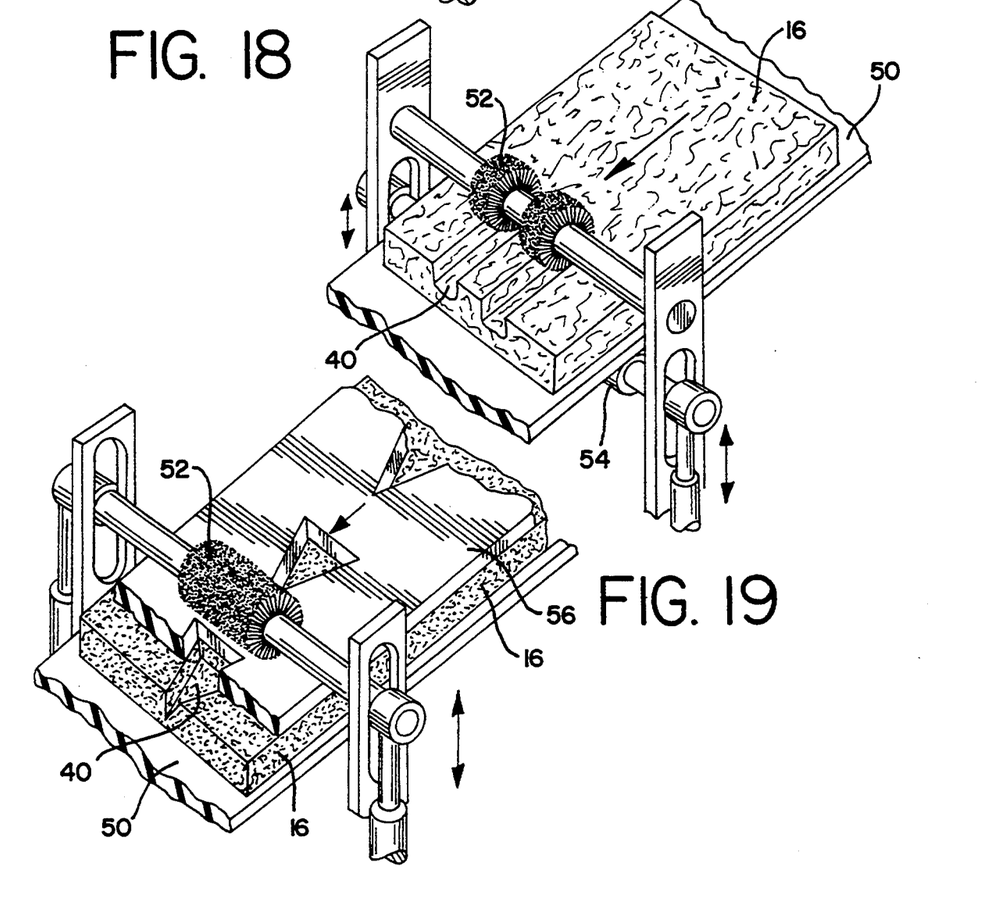

Referring to FIGS. 17–21, there is shown schematic perspective views that illustrate exemplary alternative methods of forming the elongated areas 40 in an absorbent panel 14. As shown in FIG. 17, a continuous web 16 is formed on a moving foramenous belt 50. The elongated areas 40 are formed in the web 16 by rotating a scarf roller 52. The elevation of roller 52 above belt 50 is vertically adjusted in a suitable manner to control the depth and length of the elongated areas 40 formed in the web 16. As shown in FIG. 18, the elevation of the scarf roller 52 above belt 50 may be fixed and bump roll 54 may be located below belt 50. The vertical movement of roller 54 into contact with belt 50 controls the penetration of rolls 52 into web 16. Alternatively, roller 54 may be eccentric to alter the pattern of penetration of rollers 52 into web 16.

Figure 20:
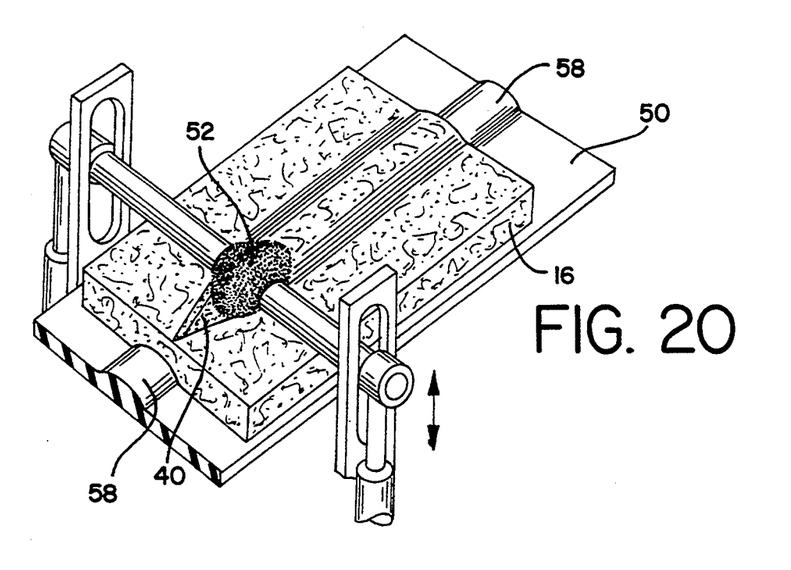
Figure 21:
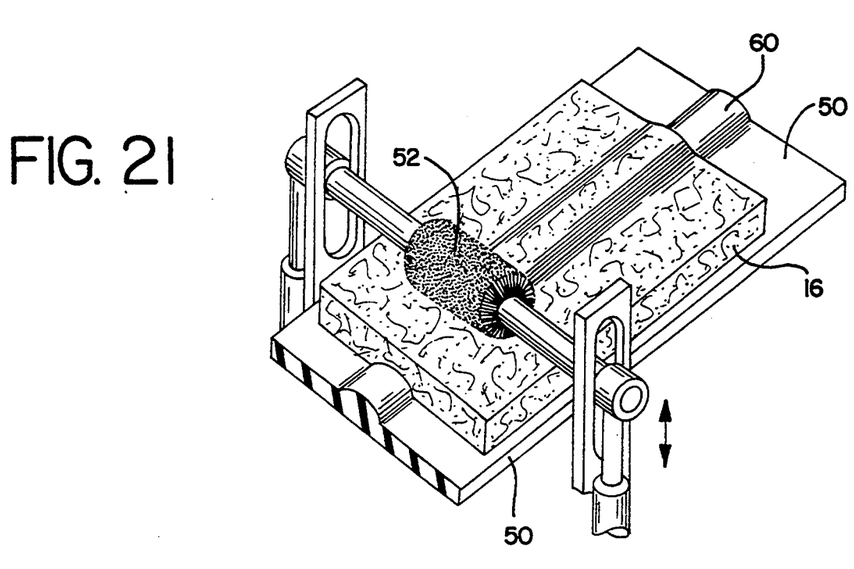

As shown in FIG. 19, the elongated areas 40 may be formed in web 16 by positioning a patterned belt 56 above web 16 that moves at the same speed as belt 50. A scarf roller 52 is positioned above belt 56 to scarf out material in the area of the cutout pattern on belt 56. Cutout portions having different lengths and shapes may be formed on belt 56. Referring to FIG. 20, a further alternative method of forming elongated areas 40 is shown wherein a cone shaped scarf roller 52 is raised and lowered toward and away from web 16 to form diamond shaped elongated areas 40. Alternatively, elongated bumps 58 may be formed on belt 50, and the elevation of the roller 52 fixed, to form the elongated diamond shaped areas. As shown in FIG. 21, the elongated areas 40 are formed in the bottom surface of web 16 by providing a hump 60 on the belt 50. A scarf roller 52 is positioned above web 16 to scarf-off the resulting top-side bump of fibers.

Although not specifically shown, the elongated areas 40 may also be formed by sprinkling a pattern of extra fiber and/or superabsorbent material onto web 16 to build-up the areas between the elongated areas. For example, conventionally known techniques for pocket forming absorbent panels (sometimes referred to as drum forming) can be employed for forming profiled absorbent structures. Such techniques can be used to create areas of differing thicknesses and fiber basis weights, which differ relative to both the length and width of the absorbent panel, in accordance with the embodiments disclosed herein.

As illustrated in FIGS. 3 and 16, the fit and esthetics of the diaper may be enhanced by laminating the top or facing sheet 12 to the elongated areas 40 of the absorbent panel 14. The absorbent panel 14 is preferably wrapped in a tissue layer 44, as is well known in the art to prevent dusting of superabsorbent particles. The elongated areas 40 may be embossed in a conventional manner and the resulting emboss lines in the panel are adhesively laminated to the tissue layer 44. The tissue layer in turn is adhesively laminated to the facing sheet 12.

In order to facilitate assembly of the absorbent panel 14 with the associated components of an absorbent garment, such as a disposable diaper, it may be desirable to direct the panel through debulking rolls, or the like, thereby subjecting the panel to compaction and densification. In so doing, the areas of increased thickness and fiber basis weight, such as at forward section 34, will be subjected to greater densification than the elongated groove areas 40, and the rearward section 36 of the panel. This results in the areas of increased thickness and basis weight exhibiting higher fiber density than the remaining areas of the absorbent panel.

Incorporation of absorbent panel structures in accordance with the present invention in a disposable diaper provides certain benefits. The disposable diaper effectively utilizes the absorbent materials in that more of the absorbent capacity is located in the vicinity of the infant voiding zone. The grooves or furrows created by the elongated areas tend to act as folding, corrugating lines when the diaper is applied and worn by the infant providing functional and aesthetic advantages. The absorbent panel structures can be readily modified to accommodate the different anthropometric needs for male and female infants with regards to maximization of location and area of absorptive capacity. Adjustments for boy/girl diaper panels could be the length and/or location of the elongated areas in conjunction with the pattern of the superabsorbent material distribution.

As discussed above, it is presently preferred that absorbent panel structures in accordance with the present invention be formed, and consist essentially of, wood pulp fluff fibers (optionally with superabsorbent material selectively dispersed therein) that are held together by interfiber bonds, without additional adhesive binders, heat-fusing of fibers, or the like. This is preferred not only for economy of materials, but additionally because of simplified manufacture, particularly facilitating formation of the elongated areas 40 of reduced thickness and basis weight. Moreover, use of interfiber bonded fibers desirably permits efficient use of superabsorbent materials, since liquid sorption and expansion (i.e., free swell) are not unnecessarily restricted or inhibited by strong fiber bonds, such as fusion or adhesive bonds. The utilization of interfiber bonded wood pulp fiber, as compared to fusion bonded thermoplastic fibers (or blends thereof) or adhesive bonded fibers, results in a structure having optimized hydrophilic properties.

From the foregoing, it will be observed that numerous modifications and corrections can be effected without departing from the true spirit and scope of the novel concept of the present invention. It will be understood that no limitation with respect to the specific embodiments illustrated herein is intended or should be inferred. It is, of course, intended to cover by the appended claims all such modifications as fall within the scope of the claims.

What is claimed is:

1. A unitary absorbent panel for a disposable garment, said panel comprising: a highly porous loosely compacted fibrous web having a forward section and a rearward section, said rearward section comprises from about 20% to about 70% of the rearward length of said panel, the fibers of said fibrous web being held together by interfiber bonds in the form of fiber-to-fiber frictional contact, a plurality of transversely spaced apart longitudinally elongated loosely compacted areas of reduced thickness and reduced basis weight in said rearward section, said elongated areas being laterally bounded by areas of increased thickness and increased basis weight, said rearward section having a mean basis weight that is from about 30% to about 70% less than the mean basis weight of a forward section of the panel that is forward of said rearward section, wherein said areas of increased thickness and increased basis weight exhibit higher fiber density than said longitudinally elongated areas of reduced thickness and basis weight, and superabsorbent particles are dispersed in at least a portion of said panel.

2. The absorbent panel as defined in claim 1 wherein said elongated areas extend to the rear edge of said panel.

3. The absorbent panel as defined in claim 1 wherein said elongated areas terminate a short distance from the rear edge of said panel.

4. The absorbent panel as defined in claim 1 wherein said elongated areas extend along substantially the entire length of said panel.

5. The absorbent panel as defined in claim 1 wherein said elongated areas extend along a section of said panel that is intermediate the front and rear edges thereof and is approximately from about 70% to about 90% of the length of said panel.

6. The absorbent panel as defined in claim 1 wherein said superabsorbent particles are substantially uniformly dispersed over substantially the entire area of said panel.

7. The absorbent panel as defined in claim 1 wherein said superabsorbent particles are dispersed in transversely spaced apart stripes that extend along the length of said panel.

8. The absorbent panel as defined in claim 7 wherein at least certain of said elongated areas coincide with at least certain of said superabsorbent-containing stripes.

9. The absorbent panel as defined in claim 7 wherein said superabsorbent-containing stripes are substantially located in the front 50% to 80% portion of said panel.

10. The absorbent panel as defined in claim 9 wherein at least certain of said elongated areas do not coincide with any of said superabsorbent-containing stripes.

11. A unitary absorbent panel for a disposable garment, said panel comprising: a highly porous loosely compacted fibrous web having a forward section and a rearward section, said rearward section comprises from about 20% to about 70% of the rearward length of said panel, the fibers of said fibrous web being held together by interfiber bonds in the form of fiber-to-fiber frictional contact, a plurality of transversely spaced apart longitudinally elongated loosely compacted areas of reduced thickness and reduced basis weight in said rearward section, said elongated areas being laterally bounded by areas of increased thickness and increased basis weight, said rearward section having a mean basis weight that is from about 30% to about 70% less than the mean basis weight of a forward section Of the panel that is forward of said rearward section, wherein said areas of increased thickness and increased basis weight exhibit higher fiber density than said longitudinally elongated areas of reduced thickness and basis weight, and the front 50-80% portion of said panel has from about 1.5 to about 4.0 times more basis weight of fibers than the rear portion of said panel.

12. The absorbent panel as defined in claim 11 wherein superabsorbent particles are dispersed in transversely spaced longitudinally stripes located in said front 50-80% portion of said panel.

13. The absorbent panel as defined in claim 11 wherein said elongated areas extend along a section of said panel that is approximately from about 70% to about 90% of the length of said panel.

14. The absorbent panel as defined in claim 12 wherein at least certain of said elongated areas do not coincide with any of said superabsorbent-containing stripes.

15. A unitary absorbent panel for a disposable garment, said panel comprising: a highly porous loosely compacted fibrous web having a forward section and a rearward section, said rearward section comprises from about 20% to about 70% of the rearward length of said panel, the fibers of said fibrous web being held together by interfiber bonds in the form of fiber-to-fiber frictional contact, a plurality of transversely spaced apart longitudinally elongated loosely compacted areas of reduced thickness and reduced basis weight in said rearward section, said elongated areas being laterally bounded by areas of increased thickness and increased basis weight, said rearward section having a mean basis weight that is from about 30% to about 70% less than the mean basis weight of a forward section of the panel that is forward of said rearward section,     wherein said areas of increased thickness and increased basis weight exhibit higher fiber density than said longitudinally elongated areas of reduced thickness and basis weight,     and said elongated areas have a thickness and a basis weight that is substantially equal over substantially the entire length thereof.

16. A unitary absorbent panel for a disposable garment, said panel comprising: a highly porous loosely compacted fibrous web having a forward section and a rearward section, said rearward section comprises from about 20% to about 70% of the rearward length of said panel, the fibers of said fibrous web being held together by interfiber bonds in the form of fiber-to-fiber frictional contact, a plurality of transversely spaced apart longitudinally elongated loosely compacted areas of reduced thickness and reduced basis weight in said rearward section, said elongated areas being laterally bounded by areas of increased thickness and increased basis weight, said rearward section having a mean basis weight that is from about 30% to about 70% less than the mean basis weight of a forward section of the panel that is forward of said rearward section,     said areas of increased thickness and increased basis weight exhibit higher fiber density than said longitudinally elongated areas of reduced thickness and basis weight,     and said elongated areas have a thickness and a basis weight that decreases as they extend toward the rear edge of said panel.

17. A unitary absorbent panel for a disposable garment, said panel comprising: a highly porous loosely compacted fibrous web having a forward section and a rearward section, said rearward section comprises from about 20% to about 70% of the rearward length of said panel, the fibers of said fibrous web being held together by interfiber bonds in the form of fiber-to-fiber frictional contact, a plurality of transversely spaced apart longitudinally elongated loosely compacted areas of reduced thickness and reduced basis weight in said rearward section, said elongated areas being laterally bounded by areas of increased thickness and increased basis weight, said rearward section having a mean basis weight that is from about 30% to about 70% less than the mean basis weight of a forward section of the panel that is forward of said rearward section, wherein said elongated areas are formed by the addition of fibers onto said fibrous web to build up the areas between said elongated areas.

18. A unitary absorbent panel for a disposable garment, said panel comprising: a highly porous loosely compacted fibrous web having a forward section and a rearward section, said rearward section comprises from about 20% to about 70% of the rearward length of said panel, the fibers of said fibrous web being held together by interfiber bonds in the form of fiber-to-fiber frictional contact, a plurality of transversely spaced apart longitudinally elongated loosely compacted areas of reduced thickness and reduced basis weight in said rearward section, said elongated areas being laterally bounded by areas of increased thickness and increased basis weight, said rearward section having a mean basis weight that is from about 30% to about 70% less than the mean basis weight of a forward section of the panel that is forward of said rearward section, wherein said elongated areas are formed during the pocket forming of the absorbent panel.

* * * * *